US009756712B2

(12) United States Patent
Wandke et al.

(10) Patent No.: US 9,756,712 B2
(45) Date of Patent: Sep. 5, 2017

(54) DEVICE FOR TREATING A SURFACE WITH A PLASMA

(71) Applicant: CINOGY GMBH, Duderstadt (DE)

(72) Inventors: Dirk Wandke, Heilbad Heiligenstadt (DE); Leonhard Trutwig, Duderstadt (DE); Mirko Hahnl, Berlingerode (DE); Karl-Otto Storck, Duderstadt (DE)

(73) Assignee: CINOGY GmbH, Duderstadt (DE)

( * ) Notice: Subject to any disclaimer, the term of this patent is extended or adjusted under 35 U.S.C. 154(b) by 0 days.

(21) Appl. No.: 15/026,359

(22) PCT Filed: Nov. 7, 2014

(86) PCT No.: PCT/DE2014/000578
§ 371 (c)(1),
(2) Date: Mar. 31, 2016

(87) PCT Pub. No.: WO2015/070835
PCT Pub. Date: May 21, 2015

(65) Prior Publication Data
US 2016/0242269 A1    Aug. 18, 2016

(30) Foreign Application Priority Data

Nov. 15, 2013   (DE) .................. 10 2013 019 058

(51) Int. Cl.
*H05H 1/24*    (2006.01)
*A61L 2/14*    (2006.01)

(52) U.S. Cl.
CPC ............. *H05H 1/2406* (2013.01); *A61L 2/14* (2013.01); *H05H 2001/2412* (2013.01); *H05H 2245/1225* (2013.01); *H05H 2277/10* (2013.01)

(58) Field of Classification Search
None
See application file for complete search history.

(56) References Cited

U.S. PATENT DOCUMENTS 5,935,460 A * 8/1999 Mori .................. B23H 1/00
219/121.39
5,948,166 A * 9/1999 David ................ C23C 16/26
118/718

(Continued)

FOREIGN PATENT DOCUMENTS

CN     102711909 A    10/2012
DE      3831964 A1     6/1989

(Continued)

*Primary Examiner* — Douglas W Owens
*Assistant Examiner* — Srinivas Sathiraju
(74) *Attorney, Agent, or Firm* — Whitham, Curtis & Cook, P.C.

(57) ABSTRACT

A device for treating a surface with a dielectric barrier plasma, wherein the surface functions as a return electrode, having a housing (1), in which a high-voltage feed line, an electrode (8) which is connected to the high-voltage feed line, and a dielectric (9), which screens the electrode (8) with respect to the surface, are located, permits the plasma treatment of highly curved surfaces and of relatively large surface areas by virtue of the fact that the electrode (8) has the shape of a circle which is mounted in the housing (1) so as to be rotatable at least to a limited degree, and projects with a spherical section from an end-side opening (5) in the housing (1), and in that the electrode (8) is coated with the dielectric (9) in such a way that its spherical section projecting out of the housing (1) is covered by the dielectric (9) in every possible rotational position.

4 Claims, 5 Drawing Sheets

(56) References Cited

U.S. PATENT DOCUMENTS

| | | | |
|---|---|---|---|
| 8,770,142 B2* | 7/2014 | Lee | C23C 16/45578 118/723 E |
| 8,851,012 B2* | 10/2014 | Lee | C23C 16/45514 118/723 E |
| 9,005,188 B2 | 4/2015 | Wandke | |
| 9,287,094 B2* | 3/2016 | Trutwig | A61L 2/14 |
| 9,498,637 B2* | 11/2016 | Mathias | A61N 1/44 |
| 2002/0026202 A1* | 2/2002 | Honey | A61B 17/221 606/127 |
| 2005/0046584 A1* | 3/2005 | Breed | B60C 11/24 340/13.31 |
| 2009/0098311 A1* | 4/2009 | Aomine | C23C 16/40 427/576 |
| 2009/0120782 A1* | 5/2009 | Hammen | B29C 59/10 204/164 |
| 2011/0022043 A1 | 1/2011 | Wandke et al. | |
| 2012/0259270 A1* | 10/2012 | Wandke | A61N 1/0408 604/23 |
| 2014/0182879 A1* | 7/2014 | Busse | A61N 1/40 174/98 |
| 2015/0216026 A1* | 7/2015 | Wandke | H05H 1/2406 313/352 |
| 2015/0343231 A1* | 12/2015 | Sanders | A61N 1/44 607/2 |
| 2015/0357163 A1* | 12/2015 | Trutwig | A61L 2/14 313/48 |

FOREIGN PATENT DOCUMENTS

| | | | |
|---|---|---|---|
| DE | 10 2007 030 915 A1 | 1/2009 | |
| DE | 10 2009 060 627 A1 | 6/2011 | |
| DE | 10 2011 105 713 A1 | 12/2012 | |
| DE | 10 2012 103 470 A1 | 10/2013 | |
| DE | 102012103470 A1 * | 10/2013 | H05H 1/2406 |
| WO | 01/87166 A2 | 11/2001 | |
| WO | 2011/076193 A1 | 6/2011 | |

* cited by examiner

DEVICE FOR TREATING A SURFACE WITH A PLASMA

FIELD OF THE INVENTION

The invention relates to a device for treating a surface with a dielectric barrier plasma, wherein the surface functions as counter electrode, comprising a housing, in which a high-voltage feed line, an electrode connected to the high-voltage feed line, and a dielectric which screens the electrode with respect to the surface are located.

BACKGROUND

A device of this type is known from DE 10 2007 030 915 A1. An elongate electrode having a cylindrical cross section and a rounded end face is surrounded here by a correspondingly formed dielectric. A surface, for example an area of skin, can be treated by the outer surface of the dielectric. A uniform treatment of a larger surface is not provided by an apparatus of this type.

In DE 10 2009 060 627, a planar electrode arrangement is provided for the treatment of larger areas of skin, in which arrangement a planar electrode is screened by a planar dielectric with respect to a surface to be treated, in particular an area of skin. For adaptation to irregular surfaces, both the electrode and the dielectric are flexible. A planar electrode of this type can be placed onto the surface to be treated, wherein the dielectric is structured so as to leave an air gap between the skin and the dielectric, in which gap the plasma discharge can take place when the surface to be treated is used as counter electrode. The disadvantage of this arrangement is the large area occupied by the electrode arrangement, which preferably can be used on a stationary unit and in addition only enables the treatment of highly curved surfaces to a limited extent.

SUMMARY

The object of the present invention is therefore to specify a device for treating a surface with a dielectric barrier plasma of the type mentioned in the introduction, with which device the plasma treatment of both highly curved surfaces and also larger surface areas is possible with simple handling.

In accordance with the invention, in order to solve this problem, a device of the type mentioned in the introduction is provided, characterized in that the electrode has the shape of a sphere which is rotatably mounted at least to a limited extent in the housing and protrudes via a spherical portion from an end-face opening in the housing, and in that the electrode is connected to the dielectric such that the spherical portion of said electrode protruding from the housing is covered by the dielectric in every possible rotational position of the electrode.

The treatment device according to the invention has only a relatively small region of contact with the surface to be treated. However, the device can be guided over the surface easily and in a controlled manner on account of the rotatably mounted spherical electrode, and therefore a plasma treatment can be performed over the surface in a controlled and uniform manner by rolling the device over the surface. Since the electrode must be connected to the high-voltage feed line within the housing of the device, the rotational movement of the spherical electrode is limited. The device according to the invention is therefore swept over the surface to be treated preferably in a meandering or spiraling manner.

The treatment device according to the invention is suitable in particular for a cosmetic treatment of the skin surface as preparation for the subsequent absorption of skincare and skin-regenerating substances applied to the skin. In addition, the treatment device according to the invention can also be used for medical purposes, for example in order to exert the antimicrobial effect of the plasma treatment on a skin surface to be treated and/or in order to prepare the skin for the improved absorption of medical active substances. The microcirculation in the tissue composite may also be positively influenced by the action of the plasma.

The dielectric surrounding the spherical electrode may have a uniform thickness—and therefore a smooth contact surface—relative to the surface to be treated, since in this case an annular region for the plasma treatment is provided around the contact surface. However, the dielectric is preferably provided with a structured surface relative to the surface to be treated, which structured surface can be formed in particular by protruding nubs, wherein the dielectric preferably has a base region of uniform thickness, from which the nubs protrude. In this way, the formation of the plasma in the gap between the nubs is ensured even in the contact region, whereby a more uniform plasma treatment is achieved. Here, the nubs form only small protrusions of up to 1 to 2 mm and are preferably spherical, wherein they can be arranged tightly together, such that the gas space is created not on account of the distance between the nubs on the surface, but on account of the spherical shape of the nubs. Between 20 and 50 nubs are preferably located on spherical portion surfaces protruding from the opening in the housing, the plane covering said nubs, i.e. connecting the maxima of the nubs, in turn forming a spherical surface corresponding to the bearing recess in the housing. The electrode is accordingly held rotatably in the housing together with the dielectric comprising the structured surface.

The device according to the invention may be fed an externally generated high voltage, wherein the high voltage is conducted in the housing of the device to the spherical electrode. However, the high voltage is preferably generated in the device itself, wherein a normal supply voltage (for example 230 V or 110 V main voltage) can be supplied via a cable. This device structure has the advantage that no high voltage is guided outside the device, and therefore the necessary device safety can be ensured much more easily.

It is also possible, however, to provide the supply voltage by means of a battery present in the device and to convert this voltage into the required high voltage. This embodiment can be utilized in particular for cosmetic applications in order to create an easily handled device having no cable connection.

In terms of design, it is advantageous when the device according to the invention can be composed of a head part and a handle part, wherein the head part comprises the electrode with the dielectric, whereas the high-voltage supply and, where applicable, the high-voltage generator and a corresponding controller are accommodated in the handle part. The head part preferably has a central connecting pin connected to the electrode, which pin projects into a complementary guide channel in the handle part in the assembled state and can be connected there to the high-voltage supply.

The connection between head part and handle part is provided preferably as a detent connection between the housing parts. In addition, a detent connection may also be provided between the connecting pin and a connecting socket contacting the connecting pin.

The insulated guide channel can be protected against an undesired, careless connection to the high-voltage feed line in that it can be closed by means of a transverse slide under spring effect, wherein the transverse slide has a through-opening, which can be brought into alignment with the guide channel by means of an actuation button, against the restoring force of the spring effect. The connection between head part and handle part is therefore possible only following the actuation of the actuation button. If the head part is removed from the handle part, i.e. for example a detent connection is detached, the transverse slide closes the guide channel on account of the spring effect, such that the high-voltage supply is covered with respect to the guide channel.

The spherical electrode can be easily assembled when the housing is formed in two parts, in particular from two half-shells, in the region supporting the spherical electrode and adjoining the opening. The spherical electrode is then inserted into the spherical portion-shaped bearing of one of the half-shells before the two half-shells are connected.

DESCRIPTION OF THE DRAWINGS

The invention will be explained in greater detail hereinafter on the basis of an exemplary embodiment illustrated in the drawing, in which.

DETAILED DESCRIPTION

Figure 1:
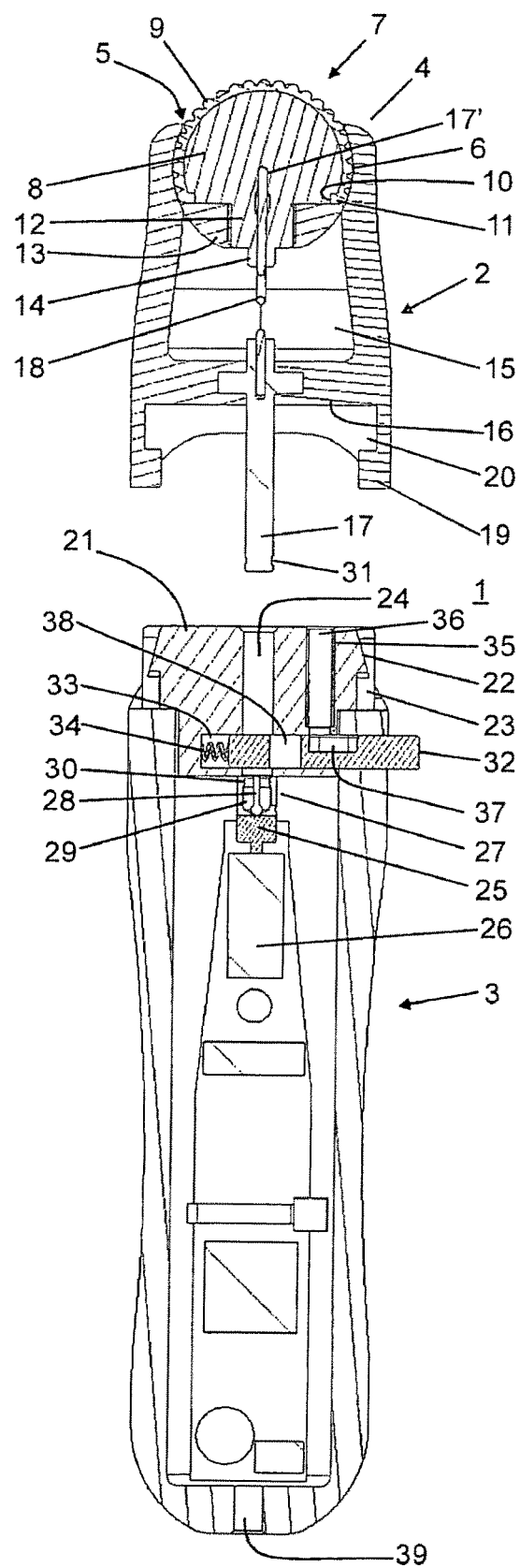
FIG. 1 shows a section in the axial direction through the housing, which consists of head part and handle part, in the unassembled state.

The device illustrated in the drawing has a housing 1, which consists of a head part 2 and a handle part 3. The head part 2 consists of a resilient plastics material and forms a one-piece wall structure, which tapers slightly conically to a free end 4. An end-face opening 5 is located in the free end. Directly behind the end-face opening 5, the wall structure of the head part 2 forms a spherical portion-shaped bearing 6, in which a spherical electrode arrangement 7 is mounted rotatably in all directions. The electrode arrangement 7 consists of an electrode 8 in sphere form, which is covered over a predominant part of its surface with a dielectric 9. The electrode arrangement 7 protrudes from the end-face opening 5 by means of a spherical portion-shaped part. The spherical portion-shaped part of the electrode arrangement 7 extends over a spherical portion, of which the height is less than ⅓, in particular less than ¼, of the diameter of the spherical electrode arrangement 7. It is thus ensured that the electrode arrangement 7, as viewed in the axial direction, is rotatably mounted in the spherical portion-shaped bearing 6 in the region of the greatest diameter of the electrode arrangement and on either side thereof over an axial length of at least ⅕ of the diameter, such that a secure mounting is ensured. The dielectric 9 extends over the spherical surface of the electrode 8 considerably over the greatest diameter of the electrode 8 with respect to the spherical portion-shaped bearing 6 and is anchored in an annular recess 10 having an annular bead 11.

On the side facing away from the end-face opening 5, the spherical electrode 8 has an annular recess, by means of which a cylindrical threaded pin is formed within the spherical contour of the electrode. A cylindrical protrusion is formed on the axial end of the threaded pin 12, which protrusion, as a stop 14, delimits the rotational movement of the spherical electrode arrangement 7 in that the stop 14 strikes against the inner wall of the head part.

The stop 14 protrudes into a hollow interior 15 of the head part 2, which interior is delimited on the one hand by the inserted electrode arrangement 7 and on the other hand by a base wall 16. A cylindrical connecting pin 17 is anchored in the base wall 16 and serves to transmit a high voltage to the electrode 8. For this purpose, the electrode 8 is provided with a channel 17 extending radially from the stop 14 to the center point, in which channel a flexible cable 18 is introduced. The other end of the cable 18 is fixedly connected to the connecting pin 17.

The housing of the head part 2 has, on the other side of the base wall 16, a peripheral edge 19 having an annular undercut 20, by means of which a detent connection to the handle part can be produced.

The substantially hollow-cylindrical handle part 3, of which the outer contour is ergonomically shaped, is terminated at its end face pointing toward the head part 2 by a substantially cylindrical insert 21 made of an insulating material. The insert has, on its outer side, a sawtooth-shaped widening 22, which is adjoined by an annular groove 23. The annular edge 19 is slid onto the sawtooth-shaped widening for assembly of the head part 2 on the handle part 3, whereby the edge 19 is expanded. With continued insertion, the edge 19 overcomes the sawtooth-shaped widening and snaps into the groove 23, whereas the sawtooth-shaped widening 22 finds space in the undercut 20, as illustrated in FIG. 2.

The insert 21 is provided with a central guide channel 24 for the connecting pin 17. At the end of the guide channel 24 facing away from the head part 2, there is located a solid cylindrical connecting piece 25, which is connected to a high-voltage generator 26 in the form of a high-voltage coil. The connecting piece 25 has a hollow-cylindrical receiving end 27, in which four slots 28 open toward the connecting pin 17 are located, which slots end at the solid region of the connecting piece 25. The slots thus delimit four clamping jaws 29, which are provided at their upper end with inwardly extending detent protrusions 30. In the assembled state (FIG. 2), in which the head part 2 is assembled on the handle part 3, the distal end of the connecting pin 17 extends into the receiving end 27 of the connecting piece 25. At its distal end, the connecting pin 17 has a peripheral detent groove 31, with which the detent beads 30 of the clamping jaws 29 engage when the head part is assembled correctly on the handle part 3. A secure high-voltage connection is ensured in this way with no risk of flashovers being produced between the high-voltage generator 26 and the electrode 8 via the connecting pin 17.

As can be seen in FIG. 1, the guide channel 24 is closed in a starting position by a transverse slide 32, which is guided in a slot transverse to the longitudinal direction of the handle part 3. The transverse slide 32 has two blind bores, in which spiral springs 34 are mounted, which are supported on an end face of the slot wall structure and in the rest state push the transverse slide 32 into the starting position illustrated in FIG. 1. The movement radially outwardly caused by the spiral springs 34 is limited by an end of a pin 36 screwed into a threaded bore 35, the end of said pin protruding into a slot-like recess 37 in the surface of the transverse slide 32 pointing toward the head part 2. The transverse slide 32 has a bore 38, which, as illustrated in FIG. 2, is aligned with the guide channel 24 when the transverse slide 32, which functions as an actuation button, is pushed inward against the force of the spiral springs 34. In this state the connecting pin 17 can be inserted into the guide slot 24 as far as the receiving end 27 of the connecting piece 25, i.e. the housing 1 can be completely assembled. If, by contrast, the head part 2 is removed, the transverse slide 32 is located in the position illustrated in FIG. 1, in which it closes the guide channel 24 with respect to the connecting piece 25 of the high-voltage generator 26 and thus provides a safety function in respect of contact with the high voltage.

Figure 2:
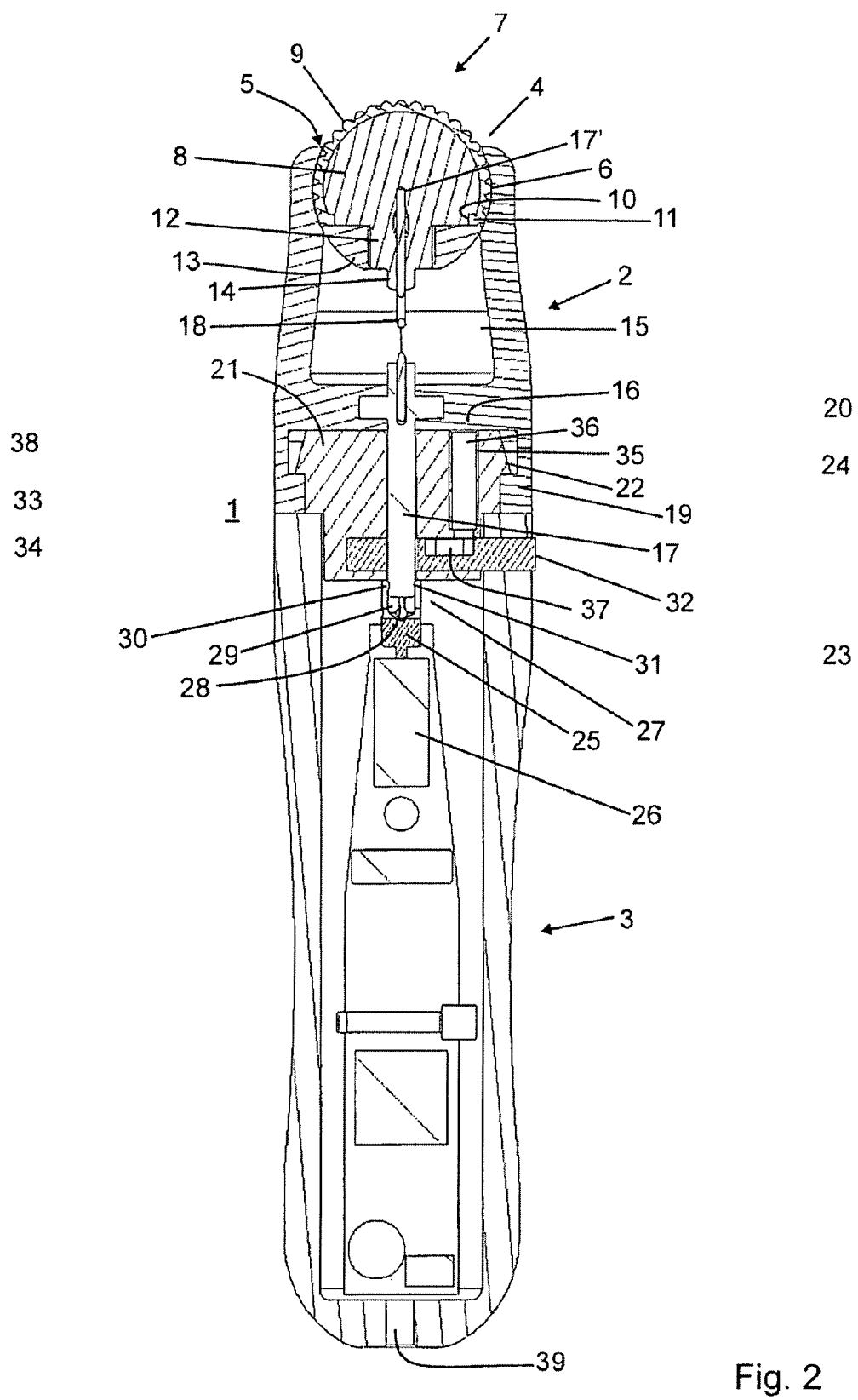
FIG. 2 shows the section according to FIG. 1 for the housing in the assembled state.

FIGS. 1 and 2 show that further components of an electronic circuit and controller are accommodated in the handle part 3. The closed end of the housing 1 opposite the insert 21 has a through-opening 39 for passing a connecting cable through. The circuit located in the handle part 3 is preferably supplied via the connecting cable with a conventional mains voltage (230 V or 110 V AC voltage) with another available supply voltage, which may also be a DC voltage. In principle, it is also conceivable to feed a high voltage already via the through-opening 39, whereby the high-voltage generator 26 in the handle part 3 could be omitted. However, the supply of a conventional mains voltage and the generation of the high voltages required for the plasma treatment by means of the high-voltage generator 26 in the housing 1 are preferred.

Provided the handle part 3 has its own power supply in the form of a battery or a rechargeable accumulator, the through-opening 39 remains unused and can be closed where appropriate.

Figure 3:
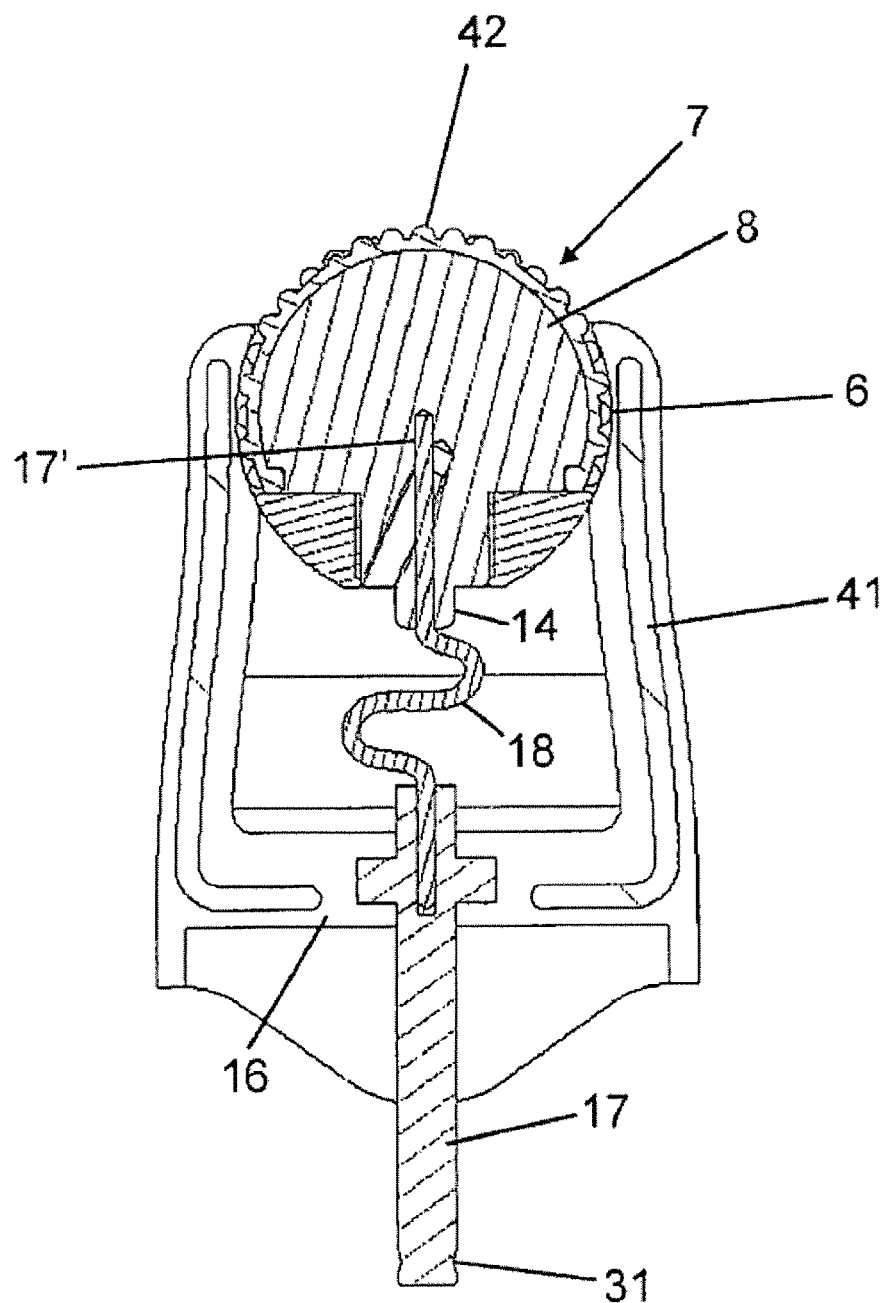
FIG. 3 shows an enlarged section perpendicularly to the plane of section from FIG. 1 through a portion of the head part of the housing.

The enlarged illustration of FIG. 3 shows that the cable 18 arranged between the connecting pin 17 and the electrode 8 is laid with an excess length in the form of a loop so that the electrode arrangement 7 can be rotated and the cable 18 can follow this rotational movement. The excess length is of such a size that the cable can take part in the rotation of the electrode arrangement 7 within the region delimited by the stop 14 so as to be tensioned.

FIG. 3 also shows that the cable end introduced through the bore 17' can be fixed by a set screw, which can be screwed into a threaded bore 40, which extends at an acute angle to the bore 17' and crosses the bore 17'.

It can also be seen in FIG. 3 that the wall structure of the head part has receiving grooves 41, which are arranged in a half-shell of the head part, as explained further below.

The enlarged illustration of FIG. 3 shows the design of the structured surface of the dielectric 9 by protruding, approximately spherical nubs 42, which are arranged practically tightly against one another and at most are distanced from one another by less than half the nub diameter.

Figure 4:
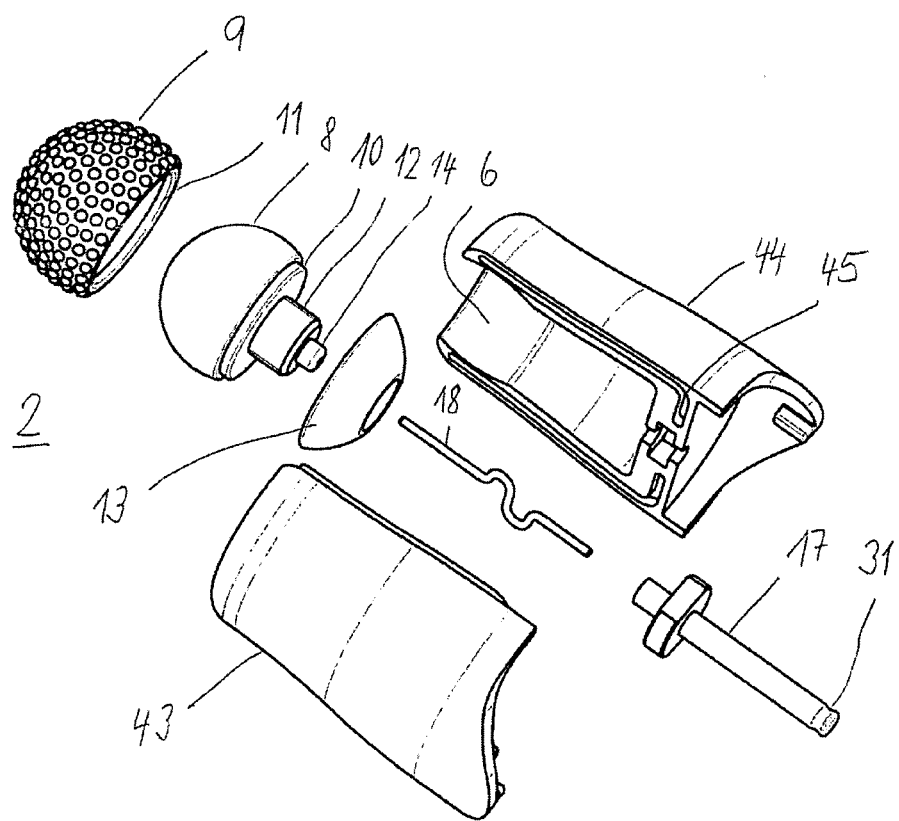
FIG. 4 shows the component parts of the head part in an exploded illustration.
Figure 5:
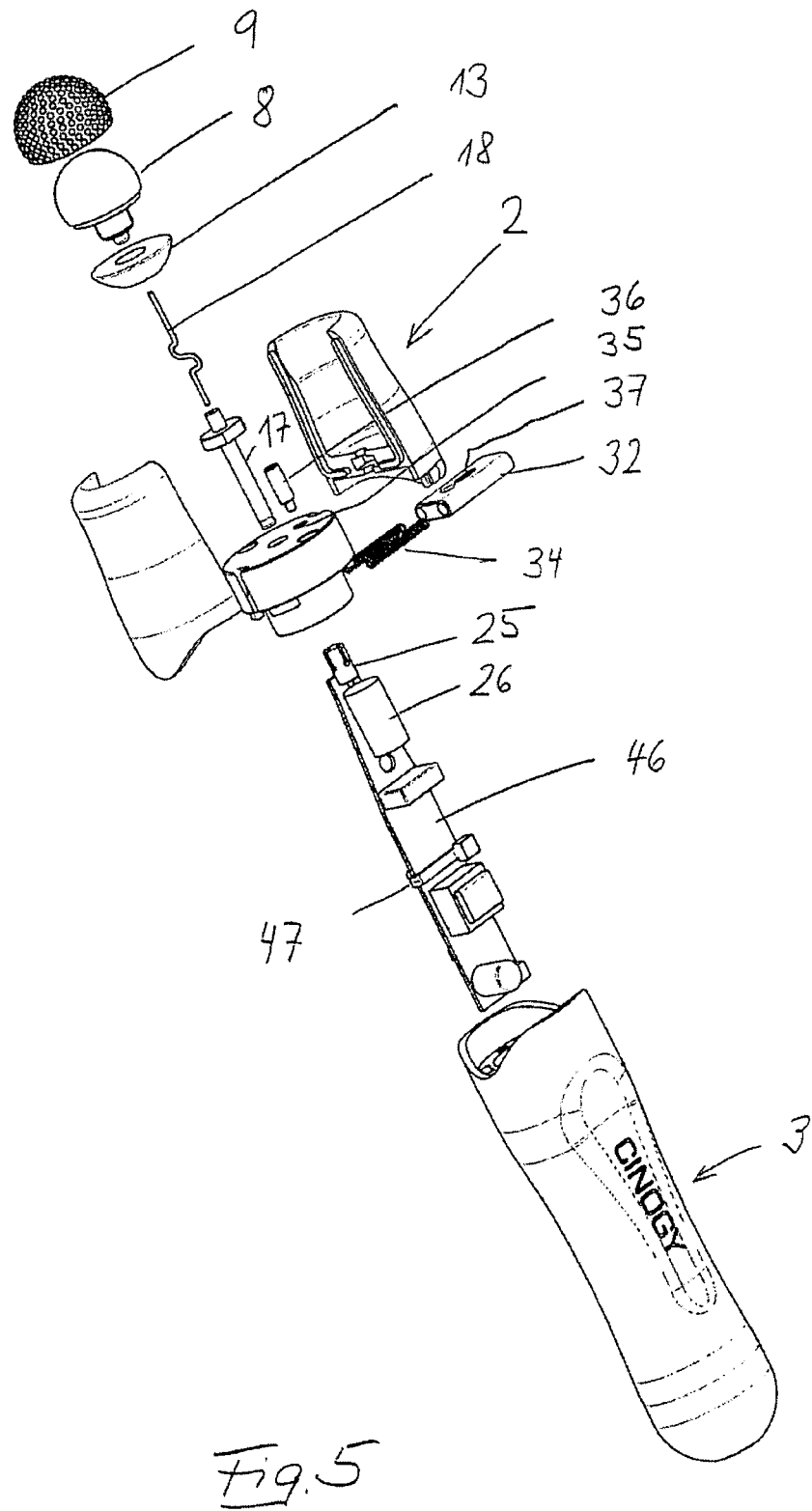
FIG. 5 shows the component parts of the entire device in an exploded illustration.

The exploded illustration of the component parts of the head part 2 in FIG. 4 shows the spherical electrode 8, which is spherical only insofar as it is rotatably mounted in the spherical portion-shaped bearing 6. An annular recess 10, the threaded pin 12, and the stop 14 are located outside this region.

The dielectric 9 is applied to the spherical part of the electrode 8, for example by shrink fitting. Here, the annular bead 11 engages with the annular recess 10 of the electrode 8. The connection thus produced between electrode 8 and dielectric 9 is secured by the closure part 13, which is screwed onto the threaded pin 12.

The dielectric 9 may also be connected to the electrode 8 by means of a coating process.

The housing of the head part 2 consists of two half-shells 43, 44, which are mirror-symmetrical, wherein the half-shell 43 comprises the receiving grooves 41, whereas the half-shell 44 is provided with a correspondingly shaped web arrangement 45, which is pressed into the receiving grooves when the two half-shells 43, 44 are pushed against one another in order to form the housing of the head part 2. The connection between the two half-shells 43, 44 can be secured by way of example by a detent means or by an adhesive bond.

The exploded illustration of the overall device shows receiving chambers 45 for the two spiral springs 34 in the transverse slide 32. It is also clear that the entire electronics system, inclusive of the high-voltage generator 36 and the connecting piece 25 is located on a printed circuit board 46, which is mounted in the handle part 3 of the housing 1 and by way of example is secured against displacement by means of a tensioning band 47.

The removable head part 2 enables a hygienic use of the device, for example in a beauty salon, with multiple people in succession, by replacement of the head part each time, such that the used head part can be cleaned and/or sterilized.

For preferred embodiments of the device according to the invention, the diameter of the electrode arrangement 7 lies between 10 and 50 mm. The height of the nubs is ≤2 mm. The thickness of the dielectric 9 (without nubs) lies preferably between 0.1 and 1 mm.

The invention claimed is:

1. A device for treating a surface with a dielectric barrier plasma, wherein the surface functions as counter electrode, comprising:
   a housing, in which a high-voltage supply an electrode connected to the high-voltage supply, and a dielectric which screens the electrode with respect to the surface are located, wherein
   the electrode has a shape of a sphere which is rotatably mounted at least to a limited extent in the housing and protrudes via a spherical portion from an end-face opening in the housing, and
   the electrode is connected to the dielectric such that the spherical portion of said electrode protruding from the housing is covered by the dielectric in every possible rotational position of the electrode, and
   wherein the housing is composed of a head part and a handle part,
   and wherein the head part comprises a connecting pin connecting to the electrode,
   wherein the connecting pin projects into a complementary guide channel in the handle part in an assembled state of the housing, and
   wherein the connecting pin is connectable to a high-voltage supply when the housing is in the assembled state.

2. The device as claimed in claim 1, wherein the dielectric has a structured surface.

3. The device as claimed in claim 2, wherein the structured surface has protruding nubs.

4. The device as claimed in claim 1, wherein the guide channel is closed by a transverse slide under spring effect, and wherein the transverse slide has a through-opening, which is alignable with the guide channel by means of an actuation button, against the restoring force of the spring effect.

* * * * *